(12) United States Patent
Bellido-Gonzalez et al.

(10) Patent No.: US 10,617,120 B2
(45) Date of Patent: Apr. 14, 2020

(54) BIO CONTROL ACTIVITY SURFACE

(71) Applicant: Gencoa Ltd., Merseyside (GB)

(72) Inventors: Victor Bellido-Gonzalez, Merseyside (GB); Dermot Patrick Monaghan, Merseyside (GB)

(73) Assignee: Gencoa Ltd., Liverpool (Merseyside) (GB)

( * ) Notice: Subject to any disclaimer, the term of this patent is extended or adjusted under 35 U.S.C. 154(b) by 0 days.

(21) Appl. No.: 14/888,242

(22) PCT Filed: Apr. 1, 2014

(86) PCT No.: PCT/GB2014/051021
§ 371 (c)(1),
(2) Date: Oct. 30, 2015

(87) PCT Pub. No.: WO2014/162125
PCT Pub. Date: Oct. 9, 2014

(65) Prior Publication Data
US 2016/0050916 A1    Feb. 25, 2016

(30) Foreign Application Priority Data

Apr. 1, 2013 (GB) .................................. 1305879.7
Apr. 4, 2013 (GB) .................................. 1306040.5

(51) Int. Cl.
*A01N 25/34* (2006.01)
*A01N 59/16* (2006.01)
(Continued)

(52) U.S. Cl.
CPC ............ *A01N 25/34* (2013.01); *A01N 59/00* (2013.01); *A01N 59/16* (2013.01); *A01N 59/20* (2013.01);
(Continued)

(58) Field of Classification Search
None
See application file for complete search history.

(56) References Cited

U.S. PATENT DOCUMENTS

2007/0003603 A1* 1/2007 Karandikar ............ A01N 59/16
424/443
2008/0292675 A1* 11/2008 Edermatt ................ A61L 15/46
514/1.1
(Continued)

FOREIGN PATENT DOCUMENTS

DE       19619287 A1    11/1997
WO    2010/088726 A1     8/2010

OTHER PUBLICATIONS

W Chen, Y Liu, HS Courtney, M Bettenga, CM Agrawal, JD Bumgardner, JL Ong. "In vitro anti-bacterial and biological properties of magnetron co-sputtered silver-containing hydroxyapatite coating." Biomaterials, vol. 27, 2006, pp. 5512-5517.*
(Continued)

*Primary Examiner* — Isaac Shomer
(74) *Attorney, Agent, or Firm* — Tanner IP PLLC; Daniel A. Tanner, III; James E. Golladay, III

(57) ABSTRACT

A bio control surface (100) comprising a substrate (5) and a first plurality of discrete, spaced-apart particles (1) disposed on the substrate (5) and a second plurality of discrete, spaced-apart particles (6) disposed on the substrate (5), wherein the first (1) and second (6) pluralities of discrete, spaced-apart particles are formed from species having different chemical and/or electrical properties. An intermediate layer (4) may be interposed between the particles (1, 6) and the substrate (5). The bio control surface (100) can be activated by exposure to particular conditions, which cause the first (1) and second (6) pluralities of particles to adopt different potentials (+, −), such that flow of charge, heat, ions
(Continued)

etc. can be used to neutralise or kill bacteria or microorganisms resident on the surface (100).

14 Claims, 4 Drawing Sheets

(51) Int. Cl.
| | |
|---|---|
| *B82Y 5/00* | (2011.01) |
| *A01N 59/00* | (2006.01) |
| *A01N 59/20* | (2006.01) |
| *C23C 16/56* | (2006.01) |
| *C23C 14/58* | (2006.01) |
| *A61L 31/16* | (2006.01) |
| *C23C 14/35* | (2006.01) |

(52) U.S. Cl.
CPC .............. *A61L 31/16* (2013.01); *B82Y 5/00* (2013.01); *C23C 14/35* (2013.01); *C23C 14/584* (2013.01); *C23C 14/5826* (2013.01); *C23C 14/5846* (2013.01); *C23C 14/5873* (2013.01); *C23C 16/56* (2013.01); *A61L 2300/404* (2013.01)

(56) References Cited

U.S. PATENT DOCUMENTS

| | | | | |
|---|---|---|---|---|
| 2008/0318366 | A1* | 12/2008 | Fournel | B81C 1/00206 438/142 |
| 2009/0220600 | A1 | 9/2009 | Parkin et al. | |
| 2009/0281635 | A1* | 11/2009 | Li | A61F 2/0045 623/23.66 |
| 2010/0112234 | A1 | 5/2010 | Spatz et al. | |
| 2010/0190004 | A1* | 7/2010 | Gibbins | A61F 13/02 428/346 |
| 2012/0164202 | A1* | 6/2012 | Harris | A47C 31/007 424/404 |
| 2012/0214172 | A1* | 8/2012 | Chen | B82Y 15/00 435/6.19 |
| 2013/0252021 | A1* | 9/2013 | Neumann | A61L 27/06 428/657 |

OTHER PUBLICATIONS

SY Lee, O Rabin. "A unique solid-solid transformation of silver nanoparticles on reactive ion-etching-processed silicon." Nanotechnology, vol. 23, 2012, pp. 1-9.*

D Lee, RE Cohen, MF Rubner. "Antibacterial Properties of Ag Nanoparticle Loaded Multilayers and Formation of Magnetically Directed Antibacterial Microparticles." Langmuir, vol. 21, 2005, pp. 9651-9659.*

"II. The Prokaryotic Cell: Bacteria." http://faculty.ccbcmd.edu/courses/bio141/lecguide/unitl/shape/shape.html, 4 printed pages, accessed May 30, 2017.*

MA Panzer, M Shandalov, JA Rowlette, Y Oshima, YW Chen, PC McIntyre, KE Goodson. "Thermal Properties of Ultrathin Hafnium Oxide Gate Dielectric Films." IEEE Electron Device Letters, vol. 30, No. 12, Dec. 2009, pp. 1269-1271. (Year: 2009).*

A Simon-Deckers, S Loo, M Mayne-L'Hermite, N Herlin-Boime, N Menguy, C Reynaud, B Gouget, M Carriere. "Size-, Composition- and Shape-Dependent Toxicological Impact of Metal Oxide Nanoparticles and Carbon Nanotubes toward Bacteria." Environmental Science and Technology, vol. 43, pp. 8423-8429. (Year: 2009).*

Y Zhou, Y Kong, S Kundu, JD Cirillo, H Liang. "Antibacterial activities of gold and silver nanoparticles against *Escherichia coli* and bacillus Calmette-Guérin." Journal of Nanobiotechnology, vol. 10:19, pp. 1-9. (Year: 2012).*

PJ Kelly, H Li, KA Whitehead, J Verran, RD Arnell, I Iordanova. "A study of the antimicrobial and tribological properties of TiN/Ag nanocomposite coatings." Surfaces & Coatings Technology, vol. 204, 2009, pp. 1137-1140. (Year: 2009).*

B Groessner-Schreiber, M Hannig, A Duck, M Griepentrog, DF Wendworth. "Do different implant surfaces exposed in the oral cavity of humans show different biofilm compositions and activities?" European Journal of Oral Science, vol. 112, 2004, pp. 516-522. (Year: 2004).*

International Search Report for PCT/GB2014/051021 dated Jul. 24, 2014.

\* cited by examiner

BIO CONTROL ACTIVITY SURFACE

This invention relates to surfaces. In particular, this invention relates to surfaces that comprise nanoscopic features; manufacturing processes for the same; and applications for surfaces and nano-deposited surfaces for bio control activity purposes.

Surface coatings and surface treatments are widely used nowadays to manipulate the chemical, physical and optical properties of surfaces compared with those of the bulk, or underlying substrate material. Coatings can be applied in a variety of ways, such as by printing processes, spray coating processes, dipping, wet chemical techniques, exposing the surface to a reactive atmosphere etc. It is also known to use physical vapour deposition (PVD) and chemical vapour deposition (CVD) techniques, such as ion bombardment, magnetron sputtering and the like to alter the surface properties of bulk materials.

PVD and CVD techniques are generally favoured where well-adhered and/or very thin coatings are required, for reasons that are well understood and documented. Moreover, PVD and CVD techniques afford a great deal of control, by variation of the process parameters, thus permitting the formation of coatings with graduated compositions, coatings that penetrate into the bulk material or substrate, and coatings having particular topographies and non-uniformities.

Active surface coatings are nowadays widely used to render the surfaces of medical devices (e.g. instruments, wound dressings, implants etc.), hand-held implements (e.g. computer keyboards, restaurant menus etc.), touch screens, hand rails, and the like antimicrobial and/or antibacterial for hygiene and anti-cross-contamination purposes. Known antibacterial or antimicrobial surfaces comprise compositions containing silver particles or silver compounds that are known to kill bacteria and the like on contact. However, the efficacy of silver-based coatings is known to deteriorate over time, and so the efficacy of the coating can likewise diminish over time. Further, whilst it is often desirable for a coating to exhibit antimicrobial or antibacterial properties permanently, there are certain applications whereby surfaces do not need to exhibit antimicrobial and antibacterial properties all of the time, or with the same activity all of the time. For example, people with certain allergies may prefer surfaces to be non-antibacterial during use, but to be able to "switch on" the antibacterial activity at will. Or, in other situations, it may be desirable for a surface to exhibit relatively low-level antibacterial characteristics for part of the time, but to exhibit relatively higher antibacterial characteristics at other times.

Existing antibacterial surfaces or surface coatings do not permit the control or switching of antibacterial activity at will. A need therefore exists for new types of surfaces and surface coatings that can overcome these, and other shortcomings, of known antibacterial and antimicrobial coatings. Further, a need exists for reliable and reproducible ways of forming such coatings and surfaces. This invention aims to provide a solution to one or more of the above problems.

Further, the optical, electrical, chemical and physical properties of nanoclusters (small particles formed from atoms or molecules) can vary enormously depending on the size, shape and other properties (e.g. size distribution, spatial distribution, inter-particle spacing etc.). On the other hand, nanoclusters at the smaller end of the size distribution can be difficult to deposit and control. A need therefore exits for a new and/or improved way of modifying the manufacturing and application of particles, and in particular, nanoclusters.

A need also exists for a new and/or improved way of controlling and/or modifying the size, adhesion, embedment, physical properties, chemical properties, optical properties, functionality, composition, density and/or patterning of nanoclusters on technical surfaces.

According to a first aspect of the invention, there is provided a bio control surface comprising a substrate and a first plurality of discrete, spaced-apart particles disposed on the substrate and a second plurality of discrete, spaced-apart particles disposed on the substrate, wherein the first and second pluralities of discrete, spaced-apart particles are formed from species having different chemical and/or electrical properties.

A second aspect of the invention provides a method of killing bacteria or microorganisms on a bio control surface, the bio control surface comprising a substrate and a first plurality of discrete, spaced-apart particles disposed on the substrate and a second plurality of discrete, spaced-apart particles disposed on the substrate, wherein the first and second pluralities of discrete, spaced-apart particles are formed from species having different chemical, physical, thermal and/or electrical properties, the method comprising the step of exposing the bio control surface to selected environmental conditions, which cause the first and second plurality of discrete, spaced-apart particles to exhibit different energy potentials, such as chemical potential, thermal potential, electrical potentials, light absorption potential, etc. whereby, in use, when a bacterium or microorganism bridges, or is interposed between, two of the spaced-apart particles, an energy pulse, such as a electromagnetic current, light emission excitation, chemical reaction, an electric current, ionic current, thermal current, flows between the said particles, via the bacterium or microorganism, thereby killing it.

Suitably, the particles comprise nanoclusters, that is to say, nanoscopic groups of atoms or compounds. The particles may be substantially monomodal, i.e. having a relatively small size distribution, or multimodal, i.e. having a relatively large size distribution. Suitably, the particles are between 0.5 nanometres and 10 micrometres in size. The particles may be smooth, rounded, irregular or facetted.

The particles may be formed from any one or more of the metals from the group comprising: gold; silver; copper; platinum, nickel, molybdenum, tin, and titanium.

The particles may be formed from any one or more of the non-metals or compounds containing elements from the group comprising: carbon; silicon; silicon carbide; titanium diboride; and titanium silicide.

The particles may be formed from any one or more of the alloys from the group comprising: Au—Cu; Au—Ag; Au—Zn; Au—Ti; Au—Si; Ag—Zn; Ag—Ti; Ag—Si; and Ag—Cu.

The particles may be formed from any one or more of the compounds from the group comprising: metal oxides; nitrides; carbides, borides, silicides, sulphates, sulphides, halogenides.

The first and second pluralities of discrete, spaced-apart particles are formed from species having different optical, light absorption, thermal, chemical and/or electrical properties. This can be accomplished by the particles being any one or more of the group comprising: formed from different materials; having different size distributions; having different shapes; being embedded by different amounts in the substrate.

As such, the first and second plurality of discrete, spaced-apart particles are suitably selected to react differently to particular or selected environmental conditions, such as, but not exclusively: exposure to reactive atmospheres; ionized and non-ionized atmospheres, exposure to reactive liquids; electromagnetic irradiation (including visible light irradiation, UV irradiation, IR irradiation, RF irradiation. Microwave irradiation); electric field, elevated temperatures; and lowered temperatures.

The presence of particles, or nanofeatures, that can respond to external activation methods such as electromagnetic radiation (e.g. IR pulses, RF pulses, microwave pulses), light (e.g. IR, UV/VIS flash), chemical activation (e.g. ozone, radicals, vapour, oxidizing or reducing agents, acid or caustic agents) and plasmas of any chemistry are also part of the present invention.

Thus, by exposing the bio control surface of the invention to selected environmental conditions, the first and second plurality of discrete, spaced-apart particles may exhibit different chemical and/or electrical responses.

In one example, the first and second plurality of discrete, spaced-apart particles are formed from different species having different electrode potentials. For example, one of the plurality of discrete, spaced-apart particles may be formed from carbon particles, whereas another plurality of discrete, spaced-apart particles may be formed from copper. Because carbon and copper, in this particular example, have different nobilities, when the bio control surface is exposed to an electrolyte, or to a reactive atmosphere, adjacent dissimilar particles will adopt different electrical potentials. Thus, if a bacterium or other pathogen is on the bio control surface bridging, or interposed between, these particles, an electrical current will flow between the particles, via the bacterium, thereby killing it.

In another example, the first plurality of discrete, spaced-apart particles are formed from carbon nanorods, and the second plurality of discrete, spaced-apart particles are formed from copper nanoparticles. In this example, when the bio control surface is exposed to an RF electrical field, the carbon nanorods and copper particles will act as antennae and an electrical current will be induced in them. Likewise, if a bacterium or other pathogen is on the bio control surface bridging, or interposed between, these particles, an electrical current will flow between the particles, via the bacterium, thereby killing it.

The presence of particles, or nanofeatures, which are able to exhibit a different chemical potential or electrical potential or quantum state or thermal state that can activate a reaction on a cell also falls within the scope of the present invention.

It will be appreciated that the number of possible combinations and permutations of materials and environments is virtually infinite, and thus it is not possible to elucidate all of the possibilities in this disclosure. However, it ought to be readily apparent from the foregoing that by providing spaced-apart particles of differing chemical and/or physical properties on a substrate, and by exposing the bio control surface to selected environmental conditions, it is possible to switch on, or off, the antibacterial and/or antimicrobial activity of the bio control surface. Moreover, it will be appreciated that more than two types of particles may be employed, and that some or all of the particles may passively or inherently exhibit antimicrobial or antibacterial properties (e.g. silver particles), but the effect of the antimicrobial or antibacterial properties can be increased (or decreased) by exposing the surface to selected environmental conditions.

A third aspect of the invention provides a method of forming a nanostructured coating on a substrate, the method comprising the steps of depositing a plurality of nanoclusters on the substrate and energetically bombarding the nanoclusters.

Suitably, the nanoclusters are dispersed on the substrate, that is to say, spaced-apart from one another. The energetic bombardment of the nanoclusters suitably does any one or more of the following: resizes the nanoclusters; improves their adhesion to the substrate; embeds, or partially embeds, them in the substrate; modifies their functionality or composition; modifies their spacing, density, dispersion, or patterning; and/or etches them.

Usually, bombardment will resize the nanoclusters creating a profile of the nanoclusters driven by the dynamics of the bombardment.

The energetic bombardment of the nanoclusters suitably occurs in a vacuum or reduced-pressure environment, for example, although not exclusively, by inverted magnetron linear ion sources. Additionally or alternatively, the energetic bombardment could be produced by reactive and non-reactive ion etching. Alternatively, the bombardment may be effected in a non-vacuum processes.

Suitably, the nanoclusters are deposited simultaneously with the energetic bombardment. Alternatively, the nanoclusters could be deposited in a separate process, spatially or temporally, to the energetic bombardment. For example, the substrate could pass through a two stage process whereby the nanoclusters are deposited initially in a first deposition step, and then subsequently energetically bombarded as they pass through a coating apparatus in accordance with the invention.

Several sequences of deposition matrix/underlayer, nanocluster, energetic bombardment and post deposition could be repeated in order to create surfaces adapted for different purposes, for example creating a multilayer structure of embedded nanoclusters. Sequences of any combination of matrix/underlayer formation, nanocluster deposition, energetic bombardment, post deposition are also part of the present invention.

Suitably, the nanoclusters are formed by a group of atoms or entities that can be separated by energetic bombardment, for example pentacene molecules, or sulphur, which could be separated in S8 and S2 molecular entities.

Suitably, the substrate comprises a matrix or underlayer, which will bond, or embed, the nanoclusters with sufficient adhesion to undergo basic energetic bombardment. The matrix or underlayer could be the same modified or unmodified substrate surface.

The nanocluster and matrix or underlayer could be formed in vacuum, gas or liquid solutions by any appropriate technique, such as electroless deposition, electrodeposition, thermal evaporation, PVD, CVD, atmospheric plasmas, plasmas and non-plasma techniques.

Suitably, the nature, chemistry, kinetic energy, mass, flux density and angle of incidence of the energetic particle bombardment could be adjustable to produce different degrees of nanocluster modification.

Sequences of any combination of matrix/underlayer formation, nanocluster deposition, energetic bombardment, post deposition are also part of the present invention.

Suitably, an apparatus for forming the surface coating comprises a feedback controller that is able to control, in an open, or in a closed, loop mode the totality or any one of the processes involved is also part of the present invention. The present invention also relates to manufacturing methods involving vacuum or non-vacuum processes. This invention also relates to the manufacturing of such devices with or without feedback process control.

The present invention also relates, to applications of such nanostructures.

According to the present invention a surface consisting of nanoclusters dispersed on a surface is subject to energetic bombardment which would create one or several, although not exclusively, of the following: resizing of the clusters, adhesion improvement, embedment, new or modified functionalities, new or modified composition, nanocluster density, dispersion, patterning, etching.

In the present invention preferably a matrix or underlayer will bond or embed the nanocluster with sufficient adhesion to undergo basic energetic bombardment. The matrix or underlayer could be the same modified or unmodified substrate surface.

According to a further aspect of the invention, there is provided a bio control surface formed by the deposition of nanofeatures on a surface or material which under self-activation or external activation or a combination of activation methods could enable, be part of, or catalyse, a chemical reaction or produce a chemical potential difference or produce an electric potential difference or a thermal potential or a quantum state able to induce decrease activity or bio deactivation or even death of a living cell or microorganism which is in proximity to, or in contact with, such nanofeatures, by chemical or by electrical conductive or by electrical capacitive or by electrical inductive or by thermal or by electromagnetic or by light radiation or by any combination of the previously mentioned methods.

In a further aspect of the invention the bio control surface could enhance bio bonding to human or animal cells when it has been applied to, for example, a medical implant or absorbable sutures or absorbable skin bandages.

Suitably, the particles are disposed on an intermediate layer deposited on the substrate. The intermediate layer suitably enhances the bonding of the particles to the substrate. In one embodiment of the invention, the substrate comprises a textile, such as a medical bandage, or a medial implant, and an interface or intermediate layer is deposited on the substrate to aid adhesion and/or bonding of the particles to the substrate.

A further aspect of the invention provides an implant, absorbable suture, bandage, or a wound dressing comprising a bio control surface as described herein. In certain particular embodiments of the invention, the implant, absorbable suture, bandage, or a wound dressing can be provided with gold or silver particles that can be IR irradiated before and after application in order to reduce infection and increase surface bonding to the surrounding tissue.

Bio control surfaces according to the invention could have their bio control properties enhanced by the application of layers and sub-layers promoting adhesion, mobility, thermal, chemical, electromagnetic properties. For example, Au based nano features deposited on, or embedded into, a heat-reflecting, or refractory, surface such as $TiO_2$ could enhance IR radiation bio control. In another example, silicon particles could be deposited on, for example, a bandage in order to create a suitable dispersive cluster growth for a subsequent Ag deposition with enhanced bio control activity. Thus, pre-treatments or pre-depositions, before the deposition of the active layer are also form part of the present invention, for example deposition of Si before the Ag clusters.

Post-treatments or post-depositions after the active layer are also part of the present invention. For example, in order to control the Ag—O interaction and bio control activity. An example of this post-treatment could be an atmospheric ozone plasma, and example of a post-deposition could be, for example, a deposition of $SiO_2$ or $SiN_x$.

Ion beam bombardment of these surfaces are also part of the present invention.

Atmospheric or low vacuum plasma application to the substrate, bonding layer or nanofeatured bio control surface area also part of the present invention.

Continuous or Pulsed frequencies of the activation from 0 Hz to 20 GHz are also part of the present invention.

Different pulsed packages are also part of the present invention.

The relative period, time on/off of each pulse could also be varied according to the present invention.

A feedback controller able to control in open loop or closed loop mode the totality or any one of the pulses is also part of the present invention.

This invention also relates to the manufacturing of such devices with or without feedback process control.

The present invention relates to the manufacturing of the device in any number of steps or processes where the substrate is any shape form such as web, glass, metal, plastic, composite, textile, fabric, tape, wire, threads, fabrics, film or any combination.

The present invention also relates, although not exclusively, to applications of any of the aforementioned nanostructures such as medical, health, food processing, food storage, sanitation, self-cleaning, self-healing applications, energy absorption, energy production, mechanical, optical, electrical, semiconductor, piezoelectric, ferroelectric, quantum dots, photovoltaic, decorative applications.

The invention shall now be further described, by way of example only, with reference to the accompanying drawings in which.

Figure 1:
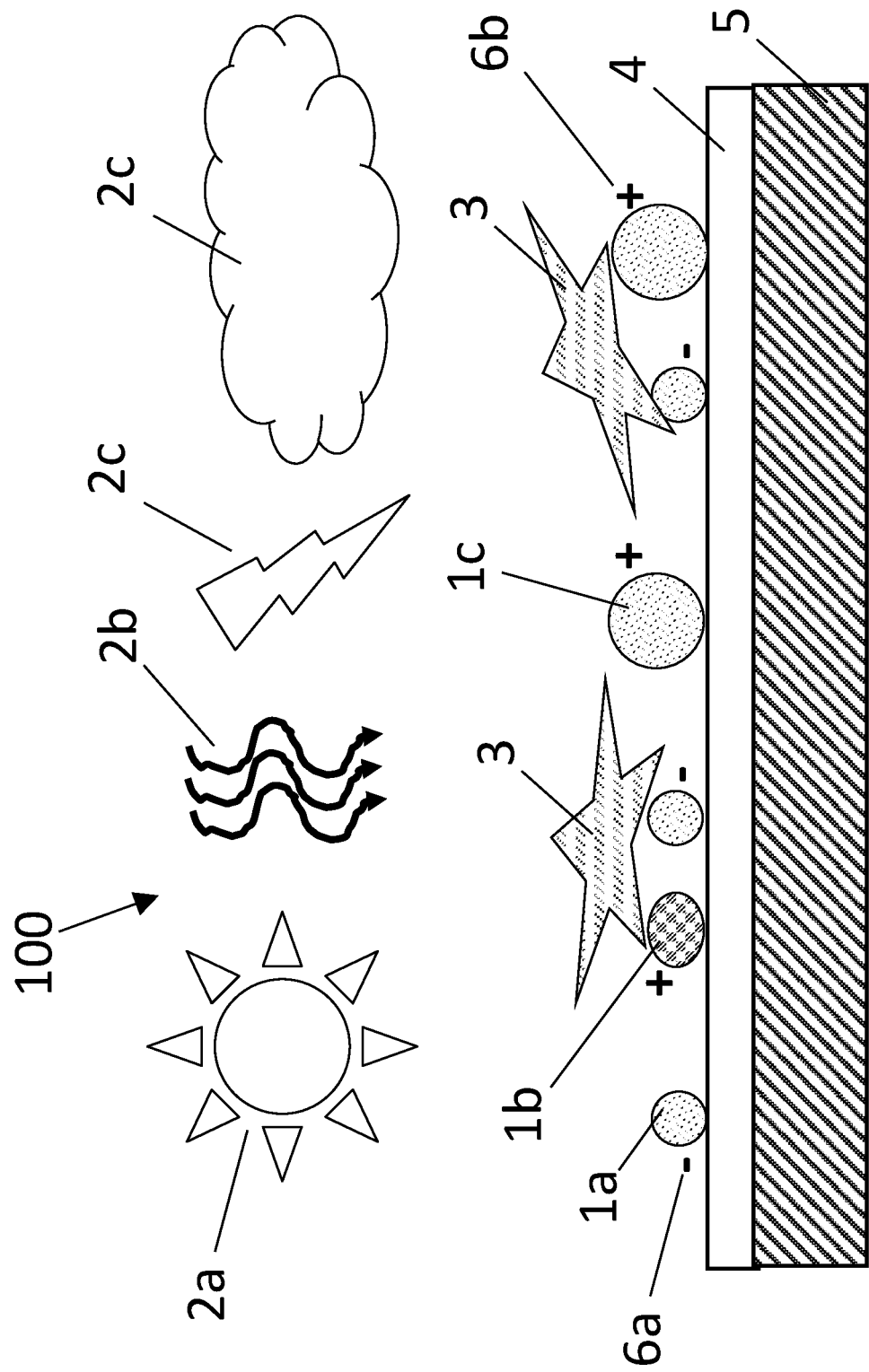
FIGS. 1 and 2 are schematic cross-sections of a bio control surface in accordance with the invention.

In FIG. 1, a bio control surface 100 in accordance with the invention comprises a plurality of spaced-apart clusters or nanofeatures 1a-c that are arranged on an intermediate layer or surface 4, which serves to facilitate anchoring the nanofeatures 1a-c to an underlying substrate 5. The intermediate layer 4 also assists the biocide function of the bio control surface 100 by enabling different potentials 6a-b, which can be different chemical potentials, different electrical potentials or different thermal potentials (temperature regions) to co-exist in different regions of the surface 4. In the illustrated example, nanofeatures 1a and 1c are made from the same material, albeit are of different sizes, whereas nanofeature 1b is made from a different material to nanofeatures 1a and 1c. Only a small portion of the bio control surface 100 has been shown, and it will be appreciated that over the surface of the bio control surface 100, there will be a great many nanofeatures of different shapes, sizes and compositions. The nanofeatures 1a-1c, which are not drawn to scale in the Figures, are typically from 0.3 nm to 10 μm in size.

Figure 2:
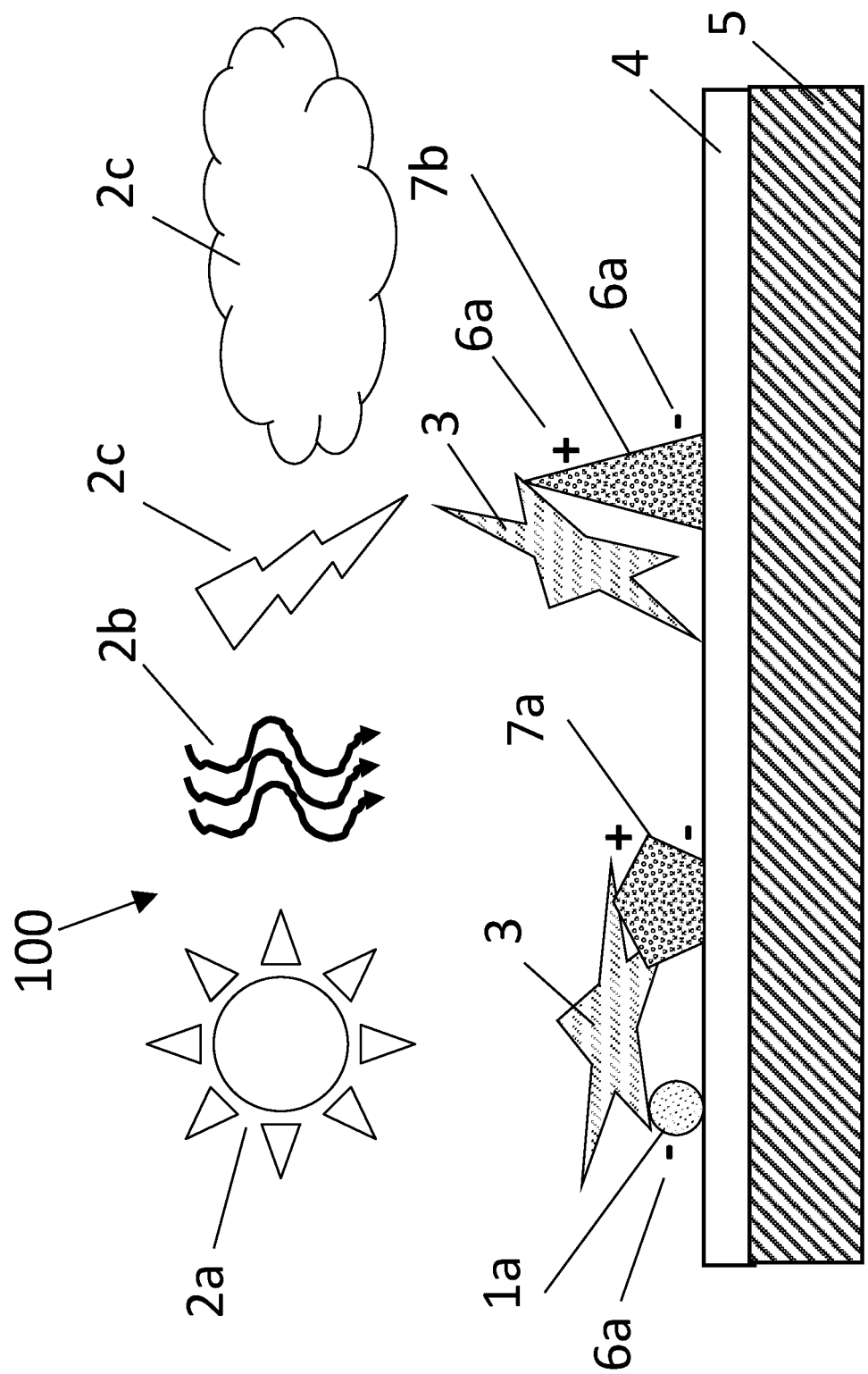

In FIGS. 1 and 2, a number of bio-organisms 3 are disposed on the bio control surface 100. The bio-organisms may be, for example, bacteria or colonies of bacteria.

Due to the spaced-apart distribution of the different nanofeatures 1a-1c on the intermediate layer 4, and due to the spacing of the nanofeatures 1a-1c being of the same order of magnitude of size of the bio-organisms 3, it will be appreciated that some of the bio-organisms 3 will bridge two or more nanofeatures 1a-1c, as shown in FIG. 1, for example, or they will bridge a nanofeature 7b and the intermediate layer 4 (of the substrate 5) as shown in FIG. 2.

Due to the dissimilarities between the nanofeatures 1a-1c, some of the nanofeatures will have a relatively high (thermal, electrical or chemical) potential, as indicated schematically by the "+" signs in the drawings, whereas other nanofeatures will have relatively lower (thermal, electrical or chemical) potentials, as indicated by the "−" signs in the drawings.

Thus, a bio-organism 3 spanning or bridging two features of regions of differing energy potential such as thermal, light absorption, chemical or electrical potential will be subjected to a respective temperature, chemical or electrical gradient. The gradient, under equilibrium conditions, creates a light emission excitations, chemical reaction, flow of heat, ions or electronic charge within the bio-organism 3, and if the flow is sufficiently high, this may be sufficient to neutralise or kill the bio-organism 3.

In other words, as a bio-organism 3 lands on, or approaches, two points or regions of the bio control surface 100 exhibiting different potentials then a reaction, chemical, electrical, electromagnetic or thermal, or combination of them can take place enabling a bio-debilitation, bio-deactivation or death of the bio-organism 3.

The activation of such function can be a self-activation, i.e. whereby under ambient conditions, the aforementioned gradient is sufficient to set up the reaction to neutralise or kill the bio-organism 3. Additionally, such reactions may be induced, or accelerated or increased by extrinsic interventions.

In FIGS. 1 and 2, it will be seen that the bio control surface 100 is exposed to light 2a, heat 2b, an electromagnetic 2c field and/or a physicochemical 2c environment. The interactions of the individual nanofeatures 1a-1c with any of the foregoing could create, increase or otherwise change the potentials (+/−) described above. Thus, the bio control surface 100 can be activated, switched on or switched off, by the exposure to, or shielding from, light 2a, heat 2b, an electromagnetic 2c field and/or a physicochemical 2c environment.

Because there are at least two types of nanofeatures, each nanofeature may interact differently with the light 2a, heat 2b, an electromagnetic 2c field and/or a physicochemical 2c environment, and thus adopt a unique potential.

FIG. 2 illustrates another example of a bio control surface 100 in accordance with the invention. FIG. 2 shows nanofeatures 1a, 7a and 7b-c arranged on a an intermediate layer 4 which serves to anchor the nanofeatures to the substrate 5 and also assist the biocide function by enabling different potentials 6a-b (either chemical, electrical, thermal to co-exist over the surface 4.

Likewise, as a bio-organism 3 approaches, or lands on two points of the surface 100 exhibiting different (chemical, thermal or electrical) potentials, then a chemical, electrical, electromagnetic, thermal (or any combination thereof) reaction can take place enabling a bio-debilitation, bio-deactivation or death of the bio-organism 3.

Again, the activation of such functionality can be a self-activation, or by continuous or pulsed induction using inducing agents such as light (IR, visible, UV) 2a, heat 2b, electrical or electromagnetic 2c fields, and/or physicochemical environments 2c.

In FIG. 2, it will be noted that the sizing and shape of the nanofeatures, such as 7a and 7b, is different, which could enable the creation of different potentials (+/−), or they may have different compositions, for example, 6a versus 7a.

Also, the height of the nanofeatures, for example, as shown schematically in 7b, could enable a potential gradient to exist across a single nanofeature 7b. In each case, the degree of activation by the ambient or extrinsic environment 2a-2c, could enable a higher of lower degree of biocide activity, as could the nature, composition, size, size distribution and shape of the nanofeatures.

Figure 3:
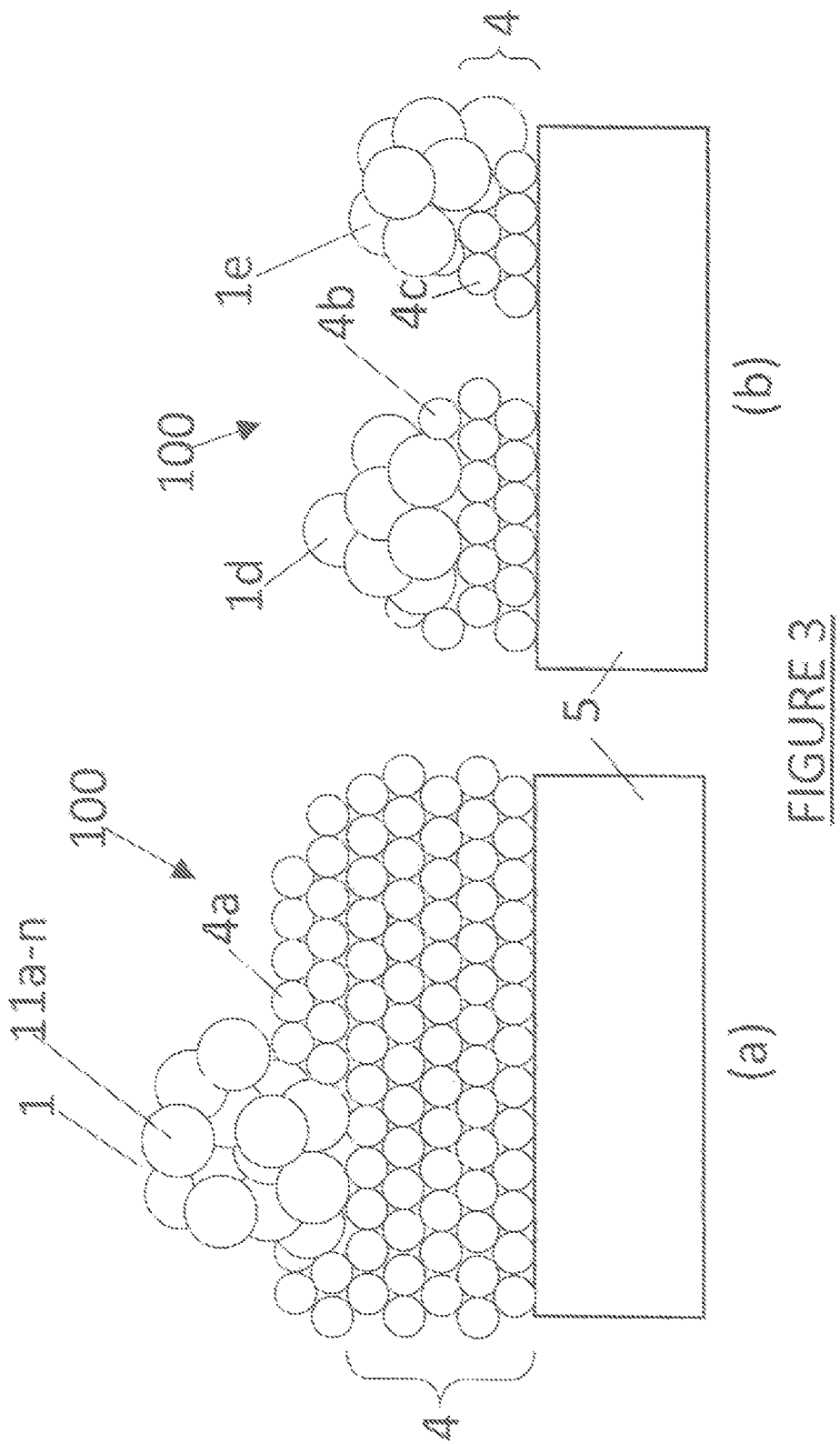
FIG. 3 is a schematic cross-section of the structure of a bio control surface in accordance with the invention.

In FIG. 3, an embodiment of the bio control surface 100 comprises a nanocluster 1 is formed by a group of atoms or distinctive entities 11a-n and a deposited surface 4 on a substrate 5, which has been formed initially (FIG. 3a) as a continuous layer of atoms or distinctive entities 4a which cover the entire, or at least the vast majority of, the surface of the substrate 5.

In FIG. 3b, it can be seen that the intermediate layer of surface 4 is discontinuous, which presents cluster-like or discrete areas 4b-4c for the nanoclusters 1d and 1e to anchor themselves to. Thus, by patterning the intermediate layer, it is possible to cause the nanoclusters to preferentially adhere to the bio control surface 100 in regions where the intermediate layer 4 exists. Thus, the patterning of the intermediate layer could be used to create the requisite spaced-apart configuration of the nanofeatures of the invention. In other words, the surface of substrate 5 is therefore covered not in its entirety by nanofeatures.

In alternative embodiments of the invention, the nanofeatures could be patterned by self-assembly techniques, e.g. by evaporating a droplet of nanofeature-containing solvent on the surface, whereby the solvent contains surfactants, ligands etc. that dictate the distribution and/or separation of the nanofeatures on the surface during evaporation of the solvent.

Figure 4:
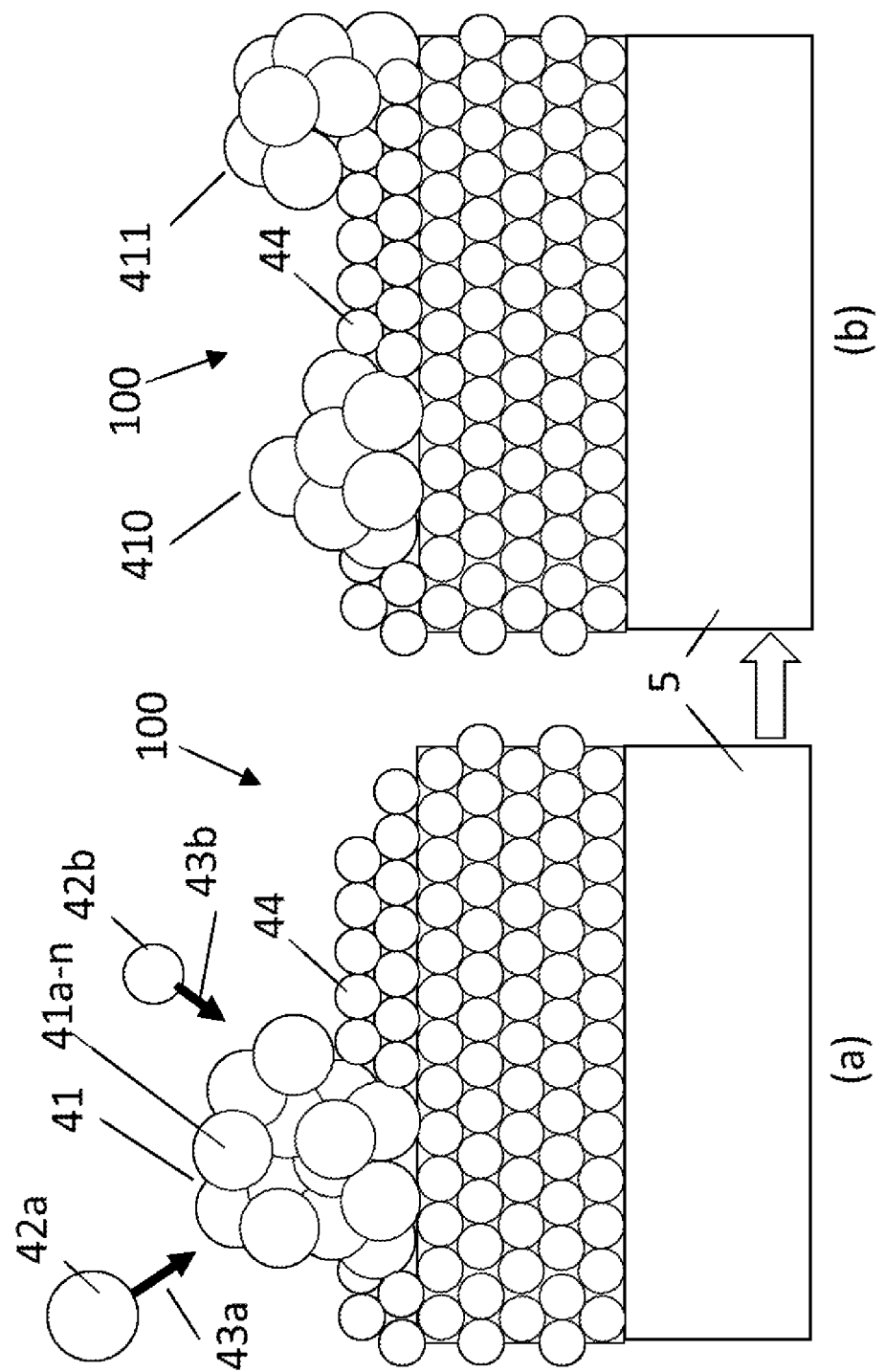
FIG. 4 is a schematic cross-section showing the formation of a bio control surface in accordance with the invention.

FIG. 4 shows a schematic of a manufacturing process for the invention. In FIG. 4a a nanocluster 41 which is formed by a group of sub-units, such as atoms, molecules or other entities 41a-n are subject to energetic bombardment by particles 42a, 42b with respective kinetic momentum 43a and 43b or energy. In FIG. 4a, the nanocluster 41 is partially embedded in matrix/underlayer 44 and the overall nanocluster 41 and matrix 44 is adhered to a substrate 5.

In FIG. 4b, it can be seen that the energetic bombardment of the nanocluster 41 by the particles 42a, 42b has broken the original cluster 41 into two smaller clusters 410, 411. Of course, the angle of incidence, kinetic momentum 43a, 43b and/or energy of the particles 42a, 42b could be varied to produce greater or lesser degrees of fragmentation of the nanocluster 41 into any number of smaller clusters 410, 411. It will also be appreciated from the foregoing that the bombardment of the surface by the energetic particles 42a, 42b may also disrupt, fragment, pattern, re-distribute or otherwise alter the matrix or intermediate layer 44, for example, to form the island or discontinuous intermediate layer as shown in FIG. 3, for example.

Further, the bombardment of the surface by the energetic particles 42a, 42b could take place simultaneously with, or subsequent to, the deposition of the nanoclusters 41. For example, a PVD or CVD process may be used, such as magnetron sputtering, whereby the nanoclusters are condensed onto the substrate 45 or intermediate layer 44 at the same time as being subjected to ion bombardment or a plasma. Such a technique may deposit and fragment the nanoclusters in any sequence or simultaneously, for example, the nanoclusters could be fragmented by the bombardment prior to attaching to the surface, or after having attached to the surface. It will also be appreciated that energetic bombardment of the nanoclusters could cause them to embed in the matrix 44 or substrate 45, as well as, or instead of, fragmenting them.

The invention is not restricted to the details of the foregoing embodiments, which are merely exemplary and/or illustrative embodiments of the invention. Various combinations and permutations of materials, processes and reactions/effects have been described herein which do not constitute an exhaustive list of such combinations or variations. Likewise, the applications of the invention are not restricted to the specific applications listed herein, and other uses for coatings, surfaces or manufacturing methods to those described herein will be apparent to those skilled in the art.

Also the invention relates to the excitation/activation methods of the biocide surface to ex-vivo such as regular decontamination of medical instruments via activation procedures described in this invention and in-vivo applications such as for example the case of prosthesis implant which is being electromagnetic radiated for biocide activation function.

The invention claimed is:

1. A bio control surface, comprising:
    a substrate;
    a first plurality of discrete, spaced-apart particles disposed on the substrate;
    a second plurality of discrete, spaced-apart particles disposed on the substrate; and
    an intermediate layer interposed between the substrate and the first plurality of discrete, spaced-apart particles and the second plurality of discrete, spaced-apart particles, the intermediate layer being discontinuous and formed of a material that assists a biocide function of the bio control surface by enabling different potentials to co-exist at different regions of the bio control surface,
    wherein:
        the first plurality of discrete, spaced-apart particles and the second plurality of discrete, spaced-apart particles are distributed on the intermediate layer with lateral spacings between the first plurality of discrete, spaced-apart particles and the second plurality of discrete, spaced-apart particles of a same order of magnitude as a size of a bacterium or microorganism, and
        the first plurality of discrete, spaced-apart particles has at least one of different chemical properties or electrical properties than the at least one of the chemical properties or electrical properties of the second plurality of discrete, spaced-apart particles, and
    the intermediate layer is manufactured of one or more of (1) an electrical insulator to enable different distributions of the first plurality of discrete, spaced-apart particles and the second plurality of discrete, spaced-apart particles to adopt different electrical potentials, (2) a thermal insulator to enable different distributions of the first plurality of discrete, spaced-apart particles and the second plurality of discrete, spaced-apart particles to adopt different temperatures, and (3) an inert material to enable different distributions of the first plurality of discrete, spaced-apart particles and the second plurality of discrete, spaced-apart particles to adopt different chemical potentials.

2. The bio control surface of claim 1, wherein the first plurality of discrete, spaced-apart particles and the second plurality of discrete, spaced-apart particles comprise any one or more of the group consisting of: nanoclusters; particles of between 0.5 nanometers and 10 nanometers in size; smooth particles; rounded particles; irregular particles; and facetted particles.

3. The bio control surface of claim 1, wherein particles in the distributions of the first plurality of discrete, spaced-apart particles and the second plurality of discrete, spaced-apart particles are formed from any one or more of the group consisting of:
    metals being one or more of the group consisting of: gold; silver; copper; platinum, nickel, molybdenum, tin, and titanium;
    non-metals being any one or more of the group consisting of: carbon; silicon; silicon carbide; titanium diboride; and titanium silicide;
    alloys being any one or more of the group consisting of: Au—Cu; Au—Ag; Au—Zn; Au—Ti; Au—Si; Ag—Zn; Ag—Ti; Ag—Si; and Ag—Cu; and
    compounds being any one or more of the group consisting of: metal oxides; nitrides; and carbides.

4. The bio control surface of claim 1, wherein the first plurality of discrete, spaced-apart particles and the second plurality of discrete, spaced-apart particles are from any one or more of groups consisting of:
    respective pluralities of the particles being of different materials;
    respective pluralities of particles having different size distributions;
    respective pluralities of particles having different shapes;
    respective pluralities of particles being embedded by different amounts in the substrate; and
    respective pluralities of particles reacting differently to at least one of particular and selected environmental conditions.

5. The bio control surface of claim 4, wherein the at least one of the particular and selected environmental conditions comprises any one or more of the group consisting of:
    a reactive atmosphere being any one or more of the group consisting of: ozone; radicals; vapour; oxidizing agents; reducing agents; acid; caustic agents; and a reactive liquid;
    an electromagnetic irradiation being any one of more of the group consisting of: visible light irradiation; UV irradiation; IR irradiation; RF irradiation; IR pulses; RF pulses; and microwave pulses; and
    an elevated temperature.

6. The bio control surface of claim 1, wherein the first plurality of discrete, spaced-apart particles and the second plurality of discrete, spaced-apart particles are formed from different materials.

7. A device, comprising:
    a bio control surface, comprising:
        a substrate;
        a first plurality of discrete, spaced-apart particles disposed on the substrate;
        a second plurality of discrete, spaced-apart particles disposed on the substrate; and
        an intermediate layer interposed between the substrate and the first plurality of discrete, spaced-apart particles and the second plurality of discrete, spaced-apart particles, the intermediate layer being discontinuous and formed of a material that assists a biocide function of the bio control surface by enabling different potentials to co-exist at different regions of the bio control surface,
    wherein:
        the first plurality of discrete, spaced-apart particles and the second plurality of discrete, spaced-apart particles are distributed on the intermediate layer with lateral spacings between the first plurality of discrete, spaced-apart particles and the second plurality of discrete, spaced-apart particles of a same order of magnitude as a size of a bacterium or microorganism, and the first plurality of discrete, spaced-apart particles has at least one of different chemical properties or electrical properties than the at least one of the chemical properties or electrical properties of the second plurality of discrete, spaced-apart particles, the device comprising any one or more of the group consisting of a medical device; a health device; a food processing device; a food storage device; a sanitation device; a self-cleaning device; a self-healing device; an energy absorption device; an energy production device; a mechanical device; an optical device; an electrical device; a semiconductor device; a piezoelectric device; a ferroelectric device; a quantum dot device; a photovoltaic device; and a decorative device.

8. The device of claim 7, wherein the device comprises a medical implant for receiving excitation energy, the device further comprising means for applying the excitation energy one of in-vivo or ex-vivo when the medical implant is inserted into a human or animal patient.

9. The device of claim 8, wherein the excitation energy is applied as a procedure (1) as a single treatment or (2) as a plurality of treatments repeated at intervals.

10. A method of forming a bio control surface the bio control surface, comprising:
   a substrate; and
   a first plurality of discrete, spaced-apart particles disposed on the substrate;
   a second plurality of discrete, spaced-apart particles disposed on the substrate; and
   an intermediate layer interposed between the substrate and the first plurality of discrete, spaced-apart particles and the second plurality of discrete, spaced-apart particles, the intermediate layer being discontinuous and formed of a material that assists a biocide function of the bio control surface by enabling different potentials to co-exist at different regions of the bio control surface, the first plurality of discrete, spaced-apart particles and the second plurality of discrete, spaced-apart particles being distributed on the intermediate layer with lateral spacings between the first plurality of discrete, spaced-apart particles and the second plurality of discrete, spaced-apart particles of a same order of magnitude as a size of a bacterium or -microorganism, and the first plurality of discrete, spaced-apart particles having at least one of different chemical properties or electrical properties than the at least one of the chemical properties or electrical properties of the second plurality of discrete, spaced-apart particles, the method comprising the step of:
   forming a nanostructured coating on the substrate by depositing a plurality of nanoclusters on the substrate;
   depositing the intermediate layer between the substrate and the nanoclusters; and
   energetically bombarding the nanoclusters,
   wherein the energetic bombardment does any one or more of the group consisting of: fragments the nanoclusters; embeds the nanoclusters; modifies the nanoclusters' functionality; modifies the nanoclusters' spacing, dispersion, or patterning; and etches the nanoclusters.

11. The method of claim 10, wherein the energetic bombardment occurs in a vacuum or reduced-pressure environment comprising an inverted magnetron linear ion source.

12. The method of claim 10, wherein the energetic bombardment is produced by reactive and non-reactive ion etching.

13. The method of claim 10, wherein the nanoclusters are deposited simultaneously with the energetic bombardment.

14. The method of claim 10, wherein the energetic bombardment at least one of fragments and distributes the intermediate layer to form a discontinuous intermediate layer to which the nanoclusters adhere.

* * * * *